(12) United States Patent
Hannigan et al.

(10) Patent No.: US 9,952,031 B1
(45) Date of Patent: Apr. 24, 2018

(54) INTERFEROMETER

(71) Applicant: University Corporation for Atmospheric Research, Boulder, CO (US)

(72) Inventors: James Hannigan, Boulder, CO (US); William Mankin, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 0 days.

(21) Appl. No.: 15/334,533

(22) Filed: Oct. 26, 2016

(51) Int. Cl.
*G01J 3/45* (2006.01)
*G01B 9/02* (2006.01)

(52) U.S. Cl.
CPC ..... *G01B 9/02015* (2013.01); *G01B 9/02043* (2013.01)

(58) Field of Classification Search
CPC ............ G01B 9/02015; G01B 9/02043; G01B 9/02044; G01B 9/02049; G01B 9/02052; G01B 9/02056; G01B 9/02059; G01J 3/45; G01J 3/4532; G01J 3/4535
USPC .................................................. 356/452, 451
See application file for complete search history.

(56) References Cited

U.S. PATENT DOCUMENTS

| | | | |
|---|---|---|---|
| 5,066,990 A | 11/1991 | Rippel | |
| 5,150,172 A | 9/1992 | Brierley | |
| 5,159,405 A | 10/1992 | Ukon | |
| 5,650,848 A * | 7/1997 | Larsson | G01J 3/453 356/455 |
| 6,075,598 A | 6/2000 | Kauppinen | |
| 6,208,424 B1 | 3/2001 | de Groot | |
| 6,229,614 B1 | 5/2001 | Larsen | |
| 2003/0048441 A1* | 3/2003 | Manning | G01J 3/453 356/326 |

OTHER PUBLICATIONS

Joel Campbell, Synthetic quadrature phrase detector/demodulator for Fourier transform spectrometers, Optical Society of America, Applied Optics, pp. 6889-6894.

* cited by examiner

*Primary Examiner* — Tarifur Chowdhury
*Assistant Examiner* — Jonathon Cook
(74) *Attorney, Agent, or Firm* — The Ollila Law Group LLC

(57) ABSTRACT

An interferometer (10) is provided that has a stage (28) configured to have a linear motion path. A first retroreflector (18) and a second retroreflector (24) are fixedly coupled to the stage (28). A tube (32) is provided, and the stage (28) is configured to reciprocate about the tube (32). A beamsplitter (14) and a 45° mirror (16) are disposed in the tube (32). A detector (22) is configured to detect light passing through the beamsplitter (14), and the beamsplitter (14) is configured to split an incident light beam into a transmitted beam (15) and a reflected beam (17), wherein the transmitted beam (15) passes to the second retroreflector (24) and the reflected beam (17) passes to the first retroreflector (18). The transmitted beam (15) and a reflected beam (17) are focused on the detector (22).

16 Claims, 2 Drawing Sheets

INTERFEROMETER

FIELD OF THE INVENTION

The embodiments described below relate to Fourier Transform Interferometers, and more particularly, to a Fourier Transform Interferometer having an improved mirror and beamsplitter arrangement.

BACKGROUND

The Michaelson Interferometer was invented in the late 1800's, and since has been widely adopted across many disciplines to create spectra from an incoming light source. Fourier Transform Interferometer based systems are used in research for assay determination, for chemical composition of samples such as for the pharmaceutical industry, on factory floors for monitoring effluent and/or air quality, etc. One application where interferometers have found particular success is in use related to detection of the infrared region of the electromagnetic spectrum. In such a role, Fourier Transform Interferometer Infra-Red (FTIR) systems may, for example, be used to measure trace gases in the earth's atmosphere.

Atmospheric measurement systems are however often employed on aircraft, and thus exposed to high levels of vibration. A fundamental design difficulty for maintaining interferometer accuracy stems from the need to maintain optical alignment of two opposing mirrors as they are physically moved when increasing the optical path difference (OPD) between them. To ensure that an interferometer remains reliable, it must be substantially immune to environmental vibrations, but this is an extremely difficult task in aircraft applications.

Typically, interferometers have a number of reflecting mirrors and two opposing retroreflectors. Generally, one of the reflecting mirrors is mounted movably in a longitudinal direction, i.e. along the path of the radiation beam, while the other is fixed. When constructing the arrangement for the movement or longitudinal displacement of the movable mirror (or reflector), effort must be made to ensure accurate displacement. Between these two mirrors is a third optical component called a beamsplitter. Attaching both mirrors to a single frame that moves relative to the beamsplitter has led to FTS systems has been introduced as a potential alignment fix, but this creates an instrument having a limited maximum optical path and/or introduces shear in the optical alignment.

The embodiments described below overcome these and other problems and an advance in the art is achieved. The embodiments described below provide an interferometer design that joins the two required mirrors in a single mechanism—a translation mirror mount that moves relative to the base housing the beamsplitter. The design of the present embodiments has no OPD limitation due to mechanical design induced shear, so an arbitrarily large OPD could be realized. Furthermore, optical misalignment introduced by a relative tilt between the base and translation mirror mount is largely self-correcting.

SUMMARY OF THE INVENTION

An interferometer is provided according to an embodiment. The interferometer comprises a stage configured to have a linear motion path and first and second retroreflectors fixedly coupled to the stage. A tube is provided, wherein the stage is configured to reciprocate about the tube. A beamsplitter and 45° mirror are disposed in the tube. A detector is configured to detect light passing through the beamsplitter; wherein the beamsplitter is configured to split an incident light beam into a transmitted beam and a reflected beam, wherein the transmitted beam passes to the second retroreflector and the reflected beam passes to the first retroreflector, and wherein the transmitted beam and a reflected beam are focused on the detector.

A method of detecting light is provided according to an embodiment. The method comprises providing a stage configured to have a linear motion path. First and second retroreflectors are fixedly coupled to the stage. A tube is provided, wherein the stage is configured to reciprocate about the tube. A beamsplitter and a 45° mirror are affixed in the tube. Light passing through the beamsplitter is detected with a detector, wherein the beamsplitter is configured to split an incident light beam into a transmitted beam and a reflected beam, wherein the transmitted beam passes to the second retroreflector and the reflected beam passes to the first retroreflector, and wherein the transmitted beam and a reflected beam are focused on the detector

Aspects

According to an aspect, an interferometer comprises: a stage configured to have a linear motion path; a first retroreflector fixedly coupled to the stage; a second retroreflector fixedly coupled to the stage; a tube, wherein the stage is configured to reciprocate about the tube; a beamsplitter disposed in the tube; a 45° mirror disposed in the tube; a detector configured to detect light passing through the beamsplitter; wherein the beamsplitter is configured to split an incident light beam into a transmitted beam and a reflected beam, wherein the transmitted beam passes to the second retroreflector and the reflected beam passes to the first retroreflector, and wherein the transmitted beam and a reflected beam are focused on the detector.

Preferably, the interferometer comprises an entry aperture defined by the tube disposed proximate the beamsplitter.

Preferably, the first retroreflector is coupled to a first side of the stage and the second retroreflector is coupled to a second side of the stage.

Preferably, the beamsplitter is disposed in a portion of the tube that projects distally from a direction of a first side of the stage, and the 45° mirror is disposed in a portion of the tube that projects distally from a direction of a second side of the stage.

Preferably, the interferometer comprises a linear drive configured to control the linear motion of the stage.

Preferably, the stage is configured to linearly move in a first direction and a second direction, wherein an optical path difference between the transmitted beam and the reflected beam increases when the stage is moved in the first direction, and wherein the optical path difference between the transmitted beam and the reflected beam decreases when the stage is moved in the second direction.

Preferably, the interferometer comprises a base.

Preferably, the base comprises a first side and a second side, and wherein the stage, the first retroreflector, the beamsplitter, the detector, and a portion of the tube that projects distally from a direction of a first side of the stage are disposed proximate the first side of the base; and the second retroreflector, 45° mirror, the detector, and a portion of the tube that projects distally from a direction of a second side of the stage are disposed proximate the second side of the base.

Preferably, the stage defines a relief to provide clearance for stage motion about the tube.

According to an aspect, a method of detecting light comprises: providing a stage configured to have a linear motion path; fixedly coupling a first retroreflector to the stage; fixedly coupling a second retroreflector to the stage; providing a tube, wherein the stage is configured to reciprocate about the tube; affixing a beamsplitter in the tube; affixing a 45° mirror in the tube; detecting light passing through the beamsplitter with a detector, wherein the beamsplitter is configured to split an incident light beam into a transmitted beam and a reflected beam, wherein the transmitted beam passes to the second retroreflector and the reflected beam passes to the first retroreflector, and wherein the transmitted beam and a reflected beam are focused on the detector.

Preferably, the method comprises providing an entry aperture on the tube proximate the beamsplitter.

Preferably, the method comprises coupling the first retroreflector to a first side of the stage; and coupling the second retroreflector to a second side of the stage.

Preferably, the method comprises coupling the beamsplitter to a portion of the tube that projects distally from a direction of a first side of the stage; and coupling the 45° mirror to a portion of the tube that projects distally from a direction of a second side of the stage.

Preferably, the method comprises coupling a linear drive to the stage to control the linear motion of the stage.

Preferably, the stage is configured to linearly move in a first direction and a second direction, wherein an optical path difference between the transmitted beam and the reflected beam increases when the stage is moved in the first direction, and wherein the optical path difference between the transmitted beam and the reflected beam decreases when the stage is moved in the second direction.

Preferably, the method comprises providing a base.

Preferably, the base comprises a first side and a second side, and wherein: the stage, the first retroreflector, the beamsplitter, the detector, and a portion of the tube that projects distally from a direction of a first side of the stage are disposed proximate the first side of the base; and the second retroreflector, 45° mirror, the detector, and a portion of the tube that projects distally from a direction of a second side of the stage are disposed proximate the second side of the base.

Preferably, stage defines a relief to provide clearance for stage motion about the tube.

BRIEF DESCRIPTION OF THE DRAWINGS

The same reference number represents the same element on all drawings. The drawings are not necessarily to scale.

DETAILED DESCRIPTION OF THE INVENTION

Figure 1:
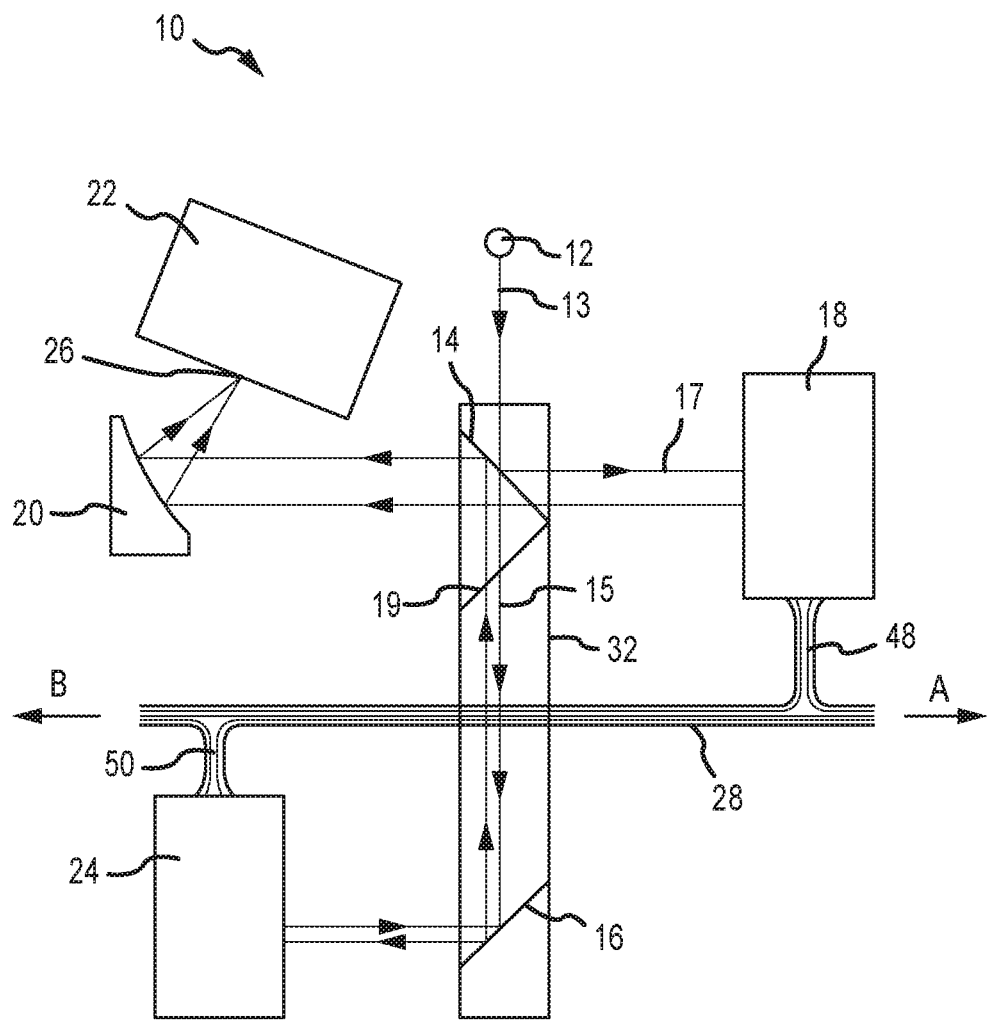
FIG. 1 is a diagram of a interferometer according to an embodiment.
Figure 2:
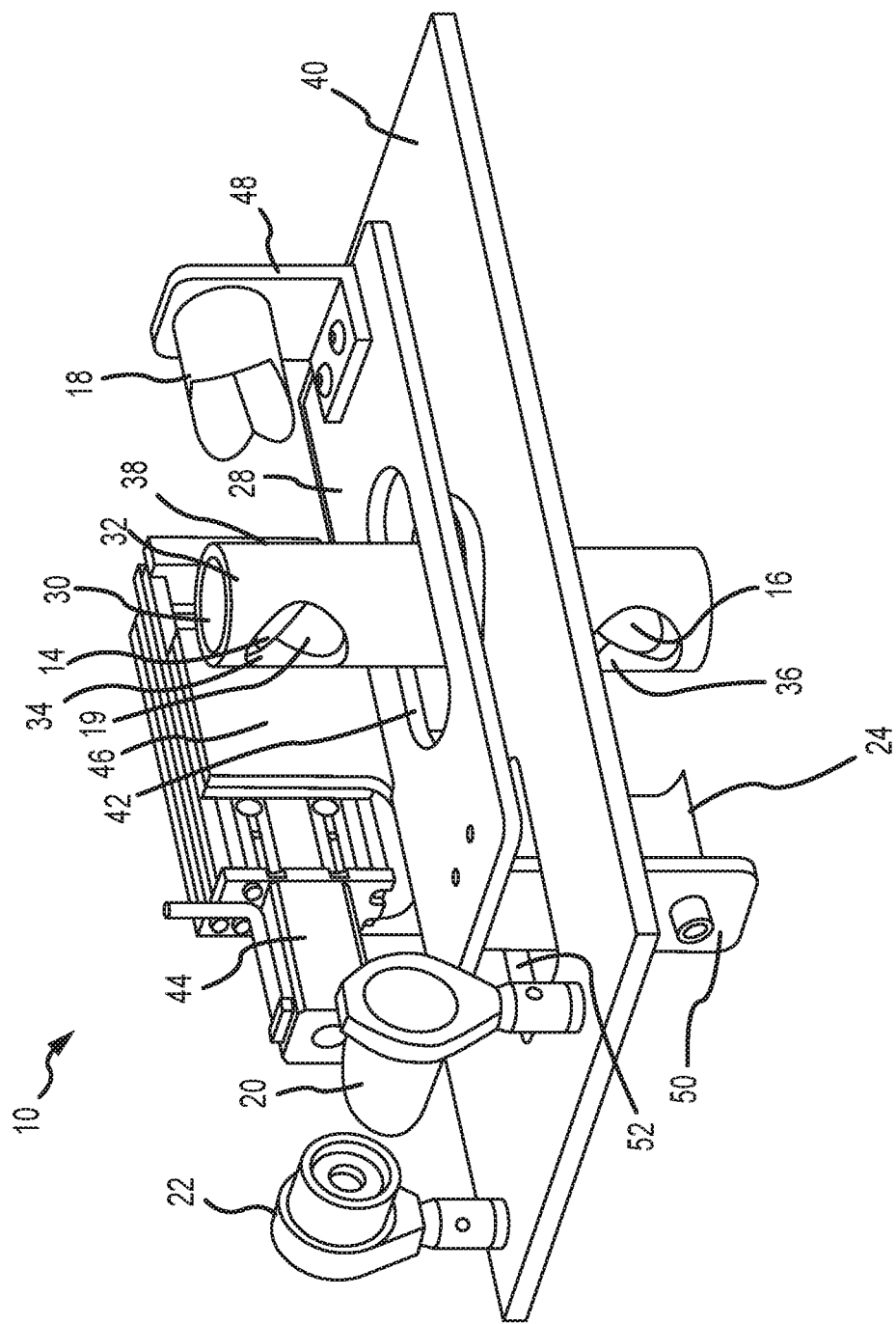
FIG. 2 illustrates an embodiment of an interferometer.

FIGS. 1 and 2 the following description depict specific examples to teach those skilled in the art how to make and use the best mode of embodiments of an interferometer and related methods. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

FIG. 1 illustrates a block diagram of an interferometer 10 according to an embodiment. Overall, the interferometer works by using a beamsplitter 14 to split an incident light beam into the two light paths (legs) of the interferometer 10. At the end of each leg is a mirror or retroreflector that reflects the light back toward the beamsplitter where the beams recombine and pass to a detection subsystem.

In particular, a light source 12 emits light beams. The light beam 13 enters a beamsplitter 14, which splits the beam into a transmitted beam 15 and a reflected beam 17. The transmitted beam 15 passes through the beamsplitter 14, and reaches a 45° mirror 16. The reflected beam 17 is reflected off the beamsplitter 14 to reach first retroreflector 18. The reflected beam 17 is reflected back from the first retroreflector 18 to pass through the beamsplitter 14.

After the transmitted beam 15 passes through the beamsplitter 14, and reaches a 45° mirror 16, the transmitted beam 15 is reflected to a second retroreflector 24. The transmitted beam 15 is then again reflected off the 45° mirror 16 to the beamsplitter 14 whereby it is reflected off the beamsplitter 14. At this point there are two beams once split and now recombined but have traveled different distances referred to as the optical path difference. The recombined beam passes to the off-axis parabolic mirror 20. The off-axis parabolic mirror 20 then reflects and focuses the recombined beam to the detector 22. Due to the focusing nature of the off-axis parabolic mirror 20, the beam arrives at a common focal point 26. The location of the focal point 26 is arranged to be on a photo-detection surface of the detector 22. Therefore, the detector 22 receives both the transmitted beam 15 and a reflected beam 17, via the off-axis parabolic mirror 20. The retroreflectors 18, 24 are mounted on a common stage 28. Overall, the legs (i.e. the transmitted beam 15 and the reflected beam 17) of the interferometer 10 have unequal light travel times or optical paths before the two split-off light beams are recombined. When recombined, the legs meet to form high-contrast fringe patterns even when the interferometer is illuminated by light from a diffuse source.

A compensator 19 may be present to make the paths of the transmitted beam 15 and the reflected beam 17 have the same optical path length when the first and second retroreflectors 18, 24 are the same distance from the beamsplitter 14.

The light fringe produced is recorded using the detector 22. One example of a detector 22 is a photomultiplier, which transduces fringe light intensity variations into voltage variations. In an embodiment, a digitizing oscilloscope or similar circuit/apparatus may be used to record the voltage variations as a function of time. The voltage-time data points collected may be analyzed by a computing device, processor, or similar digital electronics, as will be well understood by those skilled in the art.

The retroreflectors 18, 24 are illustrated as simple boxes for clarity, but each of the retroreflectors 18, 24 may comprise three reflecting plane surfaces, which are mutually perpendicular. Other focusing systems, besides an off-axis parabolic mirror 20 are contemplated, and are well-known within the art, so therefore will neither be described in this description nor shown in the drawings.

Turning to FIG. 2, the interferometer 10 is illustrated according to an embodiment. Light from a light source 12 (see FIG. 1) enters the interferometer 10 through an entry aperture 30 defined by a tube 32. The tube 32 houses both the beamsplitter 14 and the 45° mirror 16. A first aperture 34 allows light that is reflected from the 45° mirror 16 onto the beamsplitter 14 to exit the tube 32. Also, light that is reflected from the first retroreflector 18 onto the beamsplitter 14 may exit the tube 32 via the first aperture 34. A second aperture 36 allows light to pass therethrough between the 45° mirror 16 and the second retroreflector 24. Additionally, a third aperture 38 allows light to pass therethrough between the beamsplitter 14 and the first retroreflector 18. The tube 32, in an embodiment, is mounted stationarily on a base 40. The off-axis parabolic mirror 20 and the detector 22 may also be mounted on the base 40. It should be noted that the tube 32 may be constructed from a single piece of material, or may be an assembly of multiple pieces.

In an embodiment, the first and second retroreflectors 18, 24 are mounted on the stage 28. The stage 28 is configured to reciprocate along the base 40. In an embodiment, the reciprocation is along a linear motion path. In order for the first and second retroreflectors 18, 24 to maintain optical alignment with the components associated with the tube 32, a slot 42 is defined by the stage that allows the tube 32 to pass therethrough. The slot 42 provides the requisite amount clearance necessary for the stage 28 to freely reciprocate a predetermined amount. In an embodiment, the tube 32 is arranged perpendicularly to the base 40. It should be noted that the slot 42 need only be an area of clearance or relief that allows the stage 28 to move about the tube 32. In an embodiment, the stage 28 is arranged to be parallel to the base 40—therefore, the tube 32 is also perpendicular to the stage 28. The tube 32 is illustrated as having a circular cross section, but square, rounded square, and any other shape known in the art is contemplated.

The first retroreflector 18 may be attached to the stage 28 by a first standoff 48, while the second retroreflector 24 may be attached to the stage 28 by a second standoff 50. A slot 52 in the base 40 is provided to give clearance for the second standoff 50 and/or the second retroreflector 24 to pass through the base 40 in order to allow the stage 28 to reciprocate a predetermined amount. By moving the stage 28, the optical path difference (OPD) between the transmitted beam 15 and a reflected beam 17 (see FIG. 1) may be adjusted. Therefore, the stage 28 is physically moved in order to change the relative delay between the legs. A historically difficult issue in interferometer design stems from mirror mounting and the adjustments necessary to maintain optical alignment of the system. By fixing the first retroreflector 18 and/or first standoff 48 as well as the second retroreflector 24 and/or second standoff 50 to the stage 28, optical alignment may be set. Since the first retroreflector 18 and/or first standoff 48 as well as the second retroreflector 24 and/or second standoff 50 are fixedly attached to the stage 28, when the stage 28 moves, the relative alignment of the retroreflectors 18, 24 does not change.

The stage 28 may be movable by a linear drive 44. In an embodiment, the linear drive 44 is a linear actuator. Other drive mechanisms may be employed, as will be understood by those skilled in the art. In some embodiments, the stage 28 is connected directly to the linear drive 44. In some embodiments, as illustrated, a connecting member 46 attaches the stage 28 to the linear drive 44. The linear drive 44 may be electric, hydraulic, or pneumatic. It should be noted that electric, hydraulic, and pneumatic lines are not discussed for clarity, and will furthermore be well understood to those skilled in the art.

The tube 32 may be fixedly attached to the base 28. In another embodiment, tube 32 is kinematically mounted to the base 28. In either case, the beamsplitter 14 and the 45° mirror 16 also maintain a fixed position. As the stage 28 reciprocates, it moves about the tube 32, and the OPD is altered. Using FIG. 1 as a reference, as the stage 28 moves rightward (in the direction of arrow A) the length of the reflected beam 17 increases, as the first retroreflector 18 moves away from the tube 32 and beamsplitter 14. At the same time, the second retroreflector 24 moves toward the tube 32 and beamsplitter 14, so the length of transmitted beam 15 decreases. Similarly, as the stage 28 moves leftward (in the direction of arrow B), the length of the reflected beam 17 decreases, and the length of transmitted beam 15 increases. This design results in an interferometer 10 having no OPD limitation due to mechanical design induced shear. Furthermore, an arbitrarily large OPD could be realized, by adjusting the dimensions of the base 40, stage 28, the spacing of the retroreflectors 18, 24, and/or the length of the motion path of the stage 28. The design will, to an extent, self-correct optical misalignment introduced by a relative tilt between the base 40 and the standoffs 48, 50.

In an embodiment, the beamsplitter 14 and/or the compensator 19, and/or the 45° mirror 16 are kinematically mounted to the tube 32. This allows the beamsplitter/compensator/45° mirror to be adjusted, but removal and reinstallation of the tube 32 may be performed with enough optical precision to negate the need for realignment. In the case where the beamsplitter 14 and the compensator 19 and/or the 45° mirror 16 are independently adjustable, precise adjustment of the phase of the recorded interferogram may be effectuated. This reduces reliance on phase correction in the processing stream, thus increasing accuracy of the resultant spectrum.

The embodiments provided are able to be constructed small enough to be employed by unmanned aerial vehicles. In an embodiment, additional mirrors and optics are provided, as will be understood by one skilled in the art, to employ optical folding to further reduce the size of the interferometer 10 and/or increase spectral resolution.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other devices and method, and not just to the embodiments described above and shown in the accompanying figures. Accordingly, the scope of the invention should be determined from the following claims.

What is claimed is:

1. An interferometer (10) comprising:
a stage (28) configured to have a linear motion path;
a first retroreflector (18) fixedly coupled to the stage (28);
a second retroreflector (24) fixedly coupled to the stage (28);
a tube (32), wherein the stage (28) is configured to reciprocate about the tube (32);
a beamsplitter (14) disposed in a portion of the tube (32) that projects distally from a direction of a first side of the stage (28);

a 45° mirror (16) disposed in a portion of the tube that projects distally from a direction of a second side of the stage (28);

a detector (22) configured to detect light passing through the beamsplitter (14);

wherein the beamsplitter (14) is configured to split an incident light beam into a transmitted beam (15) and a reflected beam (17), wherein the transmitted beam (15) passes to the second retroreflector (24) and the reflected beam (17) passes to the first retroreflector (18), and wherein the transmitted beam (15) and a reflected beam (17) are focused on the detector (22).

2. The interferometer (10) of claim 1, further comprising: an entry aperture (30) defined by the tube (32) disposed proximate the beamsplitter (14).

3. The interferometer (10) of claim 1, wherein:
the first retroreflector (18) is coupled to a first side of the stage (28); and
the second retroreflector (24) is coupled to a second side of the stage (28).

4. The interferometer (10) of claim 1, further comprising a linear drive (44) configured to control the linear motion of the stage (28).

5. The interferometer (10) of claim 1, wherein the stage (28) is configured to linearly move in a first direction and a second direction, wherein an optical path difference between the transmitted beam (15) and the reflected beam (17) increases when the stage is moved in the first direction, and wherein the optical path difference between the transmitted beam (15) and the reflected beam (17) decreases when the stage is moved in the second direction.

6. The interferometer (10) of claim 1, further comprising a base (40).

7. The interferometer (10) of claim 6, wherein:
the base (40) comprises a first side and a second side, and wherein:
the stage (28), the first retroreflector (18), the beamsplitter (14), the detector (22), and a portion of the tube (32) that projects distally from a direction of a first side of the stage (28) are disposed proximate the first side of the base (40); and
the second retroreflector (24), 45° mirror (16), the detector (22), and a portion of the tube (32) that projects distally from a direction of a second side of the stage (28) are disposed proximate the second side of the base (40).

8. The interferometer (10) of claim 1, wherein the stage (28) defines a relief to provide clearance for stage (28) motion about the tube (32).

9. A method of detecting light comprising:
providing a stage configured to have a linear motion path;
fixedly coupling a first retroreflector to the stage;
fixedly coupling a second retroreflector to the stage;
providing a tube, wherein the stage is configured to reciprocate about the tube;
affixing a beamsplitter in a portion of the tube that projects distally from a direction of a first side of the stage;
affixing a 45° mirror in a portion of the tube that projects distally from a direction of a second side of the stage;
detecting light passing through the beamsplitter with a detector, wherein the beamsplitter is configured to split an incident light beam into a transmitted beam and a reflected beam, wherein the transmitted beam passes to the second retroreflector and the reflected beam passes to the first retroreflector, and wherein the transmitted beam and a reflected beam are focused on the detector.

10. The method of claim 9, further comprising providing an entry aperture on the tube proximate the beamsplitter.

11. The method of claim 9, further comprising:
coupling the first retroreflector to a first side of the stage; and
coupling the second retroreflector to a second side of the stage.

12. The method of claim 9, further comprising coupling a linear drive to the stage to control the linear motion of the stage.

13. The method of claim 9, wherein the stage is configured to linearly move in a first direction and a second direction, wherein an optical path difference between the transmitted beam and the reflected beam increases when the stage is moved in the first direction, and wherein the optical path difference between the transmitted beam and the reflected beam decreases when the stage is moved in the second direction.

14. The method of claim 9, further comprising providing a base.

15. The method of claim 14, wherein:
the base comprises a first side and a second side, and wherein:
the stage, the first retroreflector, the beamsplitter, the detector, and a portion of the tube that projects distally from a direction of a first side of the stage are disposed proximate the first side of the base; and
the second retroreflector, 45° mirror, the detector, and a portion of the tube that projects distally from a direction of a second side of the stage are disposed proximate the second side of the base.

16. The method of claim 9, wherein the stage defines a relief to provide clearance for stage motion about the tube.

\* \* \* \* \*

UNITED STATES PATENT AND TRADEMARK OFFICE
CERTIFICATE OF CORRECTION

| | | |
|---|---|---|
| PATENT NO. | : 9,952,031 B1 | Page 1 of 1 |
| APPLICATION NO. | : 15/334533 | |
| DATED | : April 24, 2018 | |
| INVENTOR(S) | : James Hannigan and William Mankin | |

It is certified that error appears in the above-identified patent and that said Letters Patent is hereby corrected as shown below:

In the Specification

Column 1, Line 2, insert the following statement:

--GOVERNMENT LICENSE RIGHTS
This invention was made with Government support under awards NNX13AH87G and NNX09AJ32G awarded by the National Aeronautical and Space Administration. The Government has certain rights in this invention.--

Signed and Sealed this
Seventh Day of August, 2018

Andrei Iancu
*Director of the United States Patent and Trademark Office*